US011382773B2

(12) United States Patent
Herr et al.

(10) Patent No.: US 11,382,773 B2
(45) Date of Patent: *Jul. 12, 2022

(54) BIOMIMETIC JOINT ACTUATORS

(71) Applicant: Otto Bock Healthcare LP, Austin, TX (US)

(72) Inventors: Hugh Miller Herr, Somerville, MA (US); Jeff Anthony Weber, San Francisco, CA (US); Richard James Casler, Jr., Lowell, MA (US)

(73) Assignee: Otto Bock Healthcare LP, Austin, TX (US)

( * ) Notice: Subject to any disclaimer, the term of this patent is extended or adjusted under 35 U.S.C. 154(b) by 437 days.

This patent is subject to a terminal disclaimer.

(21) Appl. No.: 16/179,789

(22) Filed: Nov. 2, 2018

(65) Prior Publication Data
US 2019/0175366 A1    Jun. 13, 2019

Related U.S. Application Data

(60) Continuation of application No. 15/877,680, filed on Jan. 23, 2018, now Pat. No. 10,143,570, which is a
(Continued)

(51) Int. Cl.
*A61F 2/66* (2006.01)
*A61F 2/64* (2006.01)
(Continued)

(52) U.S. Cl.
CPC .............. *A61F 2/66* (2013.01); *A61F 2/605* (2013.01); *A61F 2/64* (2013.01); *A61F 2/6607* (2013.01);
(Continued)

(58) Field of Classification Search
CPC ...... A61F 2/68; A61F 2/64; A61F 2002/5033; A61F 2002/6818; A61F 2002/74;
(Continued)

(56) References Cited

U.S. PATENT DOCUMENTS

| 2004/0111163 | A1* | 6/2004 | Bedard | A61F 2/644 623/33 |
| 2006/0208606 | A1* | 9/2006 | Hirzel | H02K 1/02 310/268 |
| 2009/0259320 | A1* | 10/2009 | Andrysek | A61F 2/70 623/24 |

OTHER PUBLICATIONS

Martinez-Villalpando, Ernesto. Agonist-antagonist active knee prosthesis: A preliminary study in level-ground walking. (Year: 2009).*
(Continued)

*Primary Examiner* — Christie L Bahena
(74) *Attorney, Agent, or Firm* — Goodwin Procter LLP

(57) ABSTRACT

In a powered actuator for supplying torque, joint equilibrium, and/or impedance to a joint, a motor is directly coupled to a low-reduction ratio transmission, e.g., a transmission having a gear ratio less than about 80 to 1. The motor has a low dissipation constant, e.g., less than about 50 W/(Nm)². The transmission is serially connected to an elastic element that is also coupled to the joint, thereby supplying torque, joint equilibrium, and/or impedance to the joint while minimizing the power consumption and/or acoustic noise of the actuator.

20 Claims, 5 Drawing Sheets

Related U.S. Application Data continuation of application No. 14/734,662, filed on Jun. 9, 2015, now Pat. No. 9,872,782, which is a division of application No. 13/417,949, filed on Mar. 12, 2012, now Pat. No. 9,060,883.

(60) Provisional application No. 61/451,887, filed on Mar. 11, 2011.

(51) Int. Cl.
| | | |
|---|---|---|
| *A61F 2/70* | (2006.01) | |
| *A61F 2/60* | (2006.01) | |
| *A61F 2/68* | (2006.01) | |
| *A61F 2/76* | (2006.01) | |

(52) U.S. Cl.
CPC ........ *A61F 2/70* (2013.01); *A61F 2002/6664* (2013.01); *A61F 2002/6809* (2013.01); *A61F 2002/6836* (2013.01); *A61F 2002/701* (2013.01); *A61F 2002/704* (2013.01); *A61F 2002/7625* (2013.01)

(58) Field of Classification Search
CPC .... A61F 2002/7625; A61F 2/66; A61F 2/605; A61F 2/6607; A61F 2002/701; A61F 2002/6836; A61F 2002/741; A61F 2002/6664; A61F 2002/6809; A61H 3/00; B25J 9/0006

See application file for complete search history.

(56) References Cited

OTHER PUBLICATIONS

Conrad. United States Court of Appeals. In re: Joseph Michael Conrad, III, Kurt Gans Briscoe Appellants. 2018-1659. Decided Mar. 22, 2019 (Year: 2019).*

* cited by examiner

TABLE 1: DESIGN AND OPERATION PARAMETERS

| PARAMETER | MINIMUM | TYPICAL | MAXIMUM | UNIT |
|---|---|---|---|---|
| PEAK ACTUATOR TORQUE WITHIN A GAIT CYCLE | 0.25 | 1.5 | 2.5 | NM/KG@0.75, 1.25, 3.5 M/SEC |
| JOINT VELOCITY | 1 | 2 | 3 | RAD/SEC |
| SEA FIRST RESONANCE | 12 | 50 | 100 | HZ |
| MOTOR DISSIPATION CONSTANT, $\frac{R}{K_t^2}$ ACROSS GEAR RATIO RANGE | 2 | 6 | 50 | WATTS/(NM)² |
| ACTUATOR WEIGHT | | 5.2 | | G/KG |
| TRANSMISSION GEAR (REDUCTION) RATIO | 15 | 40 | 80 | |
| BALL-SCREW PITCH | 3 | 6 | 12 | MM |
| SERIES STIFFNES (SPRING CONSTANT) AT MAXIMUM MECHANICAL POWER AMPLIFICATION | 3.0 | 4 | 4.5 | NM/RAD/KG |
| PARALLEL STIFFNESS (SPRING CONSTANT) | | 5 | | NM/RAD/KG |
| WEIGHT OF THE WEARER | 90 | 220 | 350 | LB. |

FIG. 5

BIOMIMETIC JOINT ACTUATORS

CROSS REFERENCE TO RELATED APPLICATIONS

This application is a continuation application to U.S. patent Application Ser. No. 15/877,680 filed Jan. 23, 2018, which is a continuation application to U.S. patent application Ser. No. 14/734,662, filed Jun. 9, 2015, which is a Divisional of U.S. patent application Ser. No. 13/417,949, filed Mar. 12, 2012, which claims priority to and the benefit of U.S. Provisional Patent Application Ser. No. 61/451,887, filed on Mar. 11, 2011, the contents of which are hereby incorporated by reference herein in their entirety.

FIELD OF THE INVENTION

This invention relates generally to powered human segmentation devices, such as lower-extremity prosthetic, orthotic, or exoskelton apparatus, and/or to humanoid robotic devices designed to emulate human biomechanics and to normalize function and, in particular, to device components that deliver mechanical power, and methods for controlling such components.

BACKGROUND

Superior biomimetic, lower-extremity augmentation systems and humanoid systems generally modulate mechanical impedance, joint equilibrium, and torque in accordance with gait cycle phase, walking speed, and/or terrain in a way that can emulate human behavior. In so doing, such systems can normalize or even augment metabolic cost-of-transport and self-selected walking speed with respect to average limb/joint function in a typical human. Some powered prosthetic, orthotic, and exoskeletal devices for providing and/or augmenting human joint function such that at least a biomimetic joint response is achieved have been described in co-pending U.S. patent application Ser. No. 12/157,727 "Powered Ankle-Foot Prosthesis" filed on Jun. 12, 2008 (Publication No. US2011/0257764 A1); co-pending U.S. patent application Ser. No. 12/552,013 "Hybrid Terrain-Adaptive Lower-Extremity Systems" filed on Sep. 1, 2009 (Publication No. US2010/0179668 A1); co-pending U.S. patent application Ser. No. 13/079,564 "Controlling Power in a Prosthesis or Orthosis Based on Predicted Walking Speed or Surrogate for Same" filed on Apr. 4, 2011; co-pending U.S. patent application Ser. No. 13/079,571 "Controlling Torque in a Prosthesis or Orthosis Based on a Deflection of Series Elastic Element" filed on Apr. 4, 2011; co-pending U.S. patent application Ser. No. 13/347,443 "Powered Joint Orthosis" filed on Jan. 10, 2012; co-pending U.S. patent application Ser. No. 13/356,230 "Terrain Adaptive Powered Joint Orthosis" filed on Jan. 23, 2012; and co-pending U.S. Provisional Patent Application Ser. No. 61/595,453 "Powered. Ankle Device" filed on Feb. 6, 2012, the disclosures of all of which are hereby incorporated herein in their entireties.

In these devices the torque, the impedance, and joint equilibrium are generally controlled in each joint to provide at least a biomimetic response to a wearer of the device. Specifically, these devices may provide torque in advance of toe off during a gait cycle to propel the joint. This can enable the wearer to walk faster and with less effort while at the same time improving gait mechanics, thereby mitigating the wearer's discomfort.

A series-elastic actuator (SEA), described in the above-referenced patent applications, can be used to create a backdrivable joint mechanism in prosthetic, orthotic, exoskeleton, and/or humanoid devices in which both force (torque) and impedance are controlled. Specifically, in various lower-extremity devices described in these patent applications, the SEA typically emulates the muscle-tendon unit response in an ankle, knee or hip device, specifically through implementation of a positive force or velocity feedback controller that mimics a characteristic reflex response of the joint. To this end, the SEA typically stores energy in one phase of a gait cycle (e.g., in the controlled dorsiflexion phase for an ankle device) and releases the stored energy later in the gait cycle (e.g., in the powered plantar flexion phase in the ankle device). Thus, the SEA may amplify the peak power of the actuator, thereby reducing the size and weight of the motor and the transmission. As such, devices employing an SEA may both require less battery power and produce less acoustic noise than other robotic systems that provide torque for propelling a joint, but that do not use an SEA. Nevertheless, the devices using an SEA (as well as those not using an SEA) can still require substantial battery power and may produce noise that is unacceptable to some users in certain situations.

One of the reasons for the high power consumption and noise is that conventional electric actuators in leg prosthetic, orthotic, and exoskeletal devices generally employ low-torque, high-speed (i.e., high revolutions per minute (RPM) motors that are light weight but are limited in their torque capability. For example, the EC-4Pole 30 Maxon Motor that may be employed in prosthetic and/or orthotic devices has a low-mass (about 300 grams), but has a rather modest torque capability of about 0.12 Newton-meter continuous tongue, and a relatively high speed (about 16,500 RPM zero-load speed). To achieve the high joint torque and low speed required to emulate the dynamics of a biological leg joint using a low torque, high RPM motor, a transmission having a large reduction ratio (e.g., greater than about 150:1) is generally needed. Transmissions having such high reduction ratios, when used in an actuator system to emulate the biological dynamics of ankle, knee, and/or hip joints, typically produce significant acoustic noise output. Such transmissions may also have large frictional losses and may have low backdrivability.

A high acoustic output may draw attention to the wearer of the device, and can thus be uncomfortable or embarrassing in certain social situations. Moreover, high friction and poor backdrivability can result in a relatively poor transmission efficiency, increasing the power consumption of the device. These two parameters can also adversely affect the overall control of the joint, whether for adjusting the joint position or for applying impedance and/or force/torque. In addition, high transmission ratios can be difficult to achieve and often require many functional pasts, which limits system cycle life and increases manufacturing complexities and associated costs. Therefore, there is a need for improved powered actuators for use in prosthetic, orthotic, exoskeleton, and/or humanoid devices.

SUMMARY

In various embodiments, the present invention provides powered actuator devices and methods for operating/controlling such actuators so that human augmentation devices using these actuators can accurately modulate the torque, joint equilibrium, and impedance applied to a human joint, while significantly reducing the power consumption and acoustic noise of the powered actuators. This is achieved, in part, by using a high torque, low RPM motor that is directly coupled to a highly backdrivable, low friction, low-reduction ratio transmission, and by using an elastic element, coupled in series with the transmission, coupling the joint to which torque/impedance is to be supplied with the transmission.

Conventional actuators typically employ high-rpm motors and high gear-ratio transmissions using timing belts and gears, which can generate acoustic noise and dissipate power. In various powered actuators described herein, an efficient, high-torque motor, such as a transverse flux motor, having low thermal dissipation is coupled directly to a low gear-ratio transmission, e.g., a transmission having a reduction ratio of about 80:1 or less. Examples of such transmissions include ball-screw and cable transmissions. These actuators are thus directly coupled to the robotic joint, via an elastic element coupled in series with the low-reduction transmission, delivering high-torque with low inertia and high efficiency to the joint. As these actuators eliminate the belts and gears used in conventional transmissions, they can be more durable, light-weight quiet, backdrivable, powerful, efficient, and scalable, compared to the conventional actuators.

These improved SEAs may be employed to emulate the behavior of human muscles and tendons. In general, low acoustic noise, force and impedance controllability, and high efficiency are important attributes of biological muscle-tendon units. An SEA including a high torque, low RPM motor (e.g., a transverse-flux motor), a low-reduction ratio transmission directly coupled to the motor, and tendon-like elastic element coupled in series with the transmission can provide many of these attributes of biological muscle-tendon units with greater efficacy compared to traditional actuator designs currently employed in wearable robotic systems. This particular combination of mechanical and electromechanical elements in the improved SEAs facilitates a biomimetic actuator platform capable of emulating the natural dynamics of biological leg joints in tasks such as walking, stair climbing/descending, and running, at high efficiency and controllability with relatively low acoustic noise output.

Accordingly, in one aspect, embodiments of the invention feature a powered actuator for supplying one or more of an augmentation torque, joint equilibrium, and an impedance to a joint augmented by a powered human augmentation device. The powered actuator includes a motor having a dissipation constant less than about 50 W/(Nm)$^2$, and a transmission coupled directly to the motor. The powered actuator also includes an elastic element coupled to the joint that is also coupled, in series, to the transmission. The powered actuator, as adapted for use in an ankle, can generate a normalized joint torque in a range from about −2.8 to about 2.8 Nm/kg.

In some embodiments, the motor may include a high-torque motor supplying motor torque of at least about 0.06 Nm/kg. Alternatively, or in addition, the motor may include a low revolutions per minute (RPM) motor having an RPM less than about 1500, a transverse-flux motor, or both. The actuator may be adapted to be backdrivable.

In some embodiments, the transmission has a gear ratio less than about 80:1. The transmission may include a ball-screw transmission having a ball nut coupled to the elastic element. The ball-screw transmission may include a screw having a pitch in a range of about 2 mm up to about 10 mm, which can yield the gear ratio of less than about 80:1.

In some embodiments, the elastic element may include a spring, and the powered actuator may additionally include a cable and a joint output pulley. In those embodiments, the cable is coupled to both the spring and the joint output pulley. In some other embodiments, the transmission includes a ball-screw transmission having a ball nut coupled to the motor rotor and the screw is coupled to the elastic element.

In some embodiments, the motor of the powered actuator includes a motor having an external rotor, and the transmission includes a cable and a joint output pulley. The cable couples the external rotor and the joint output pulley. The cable may be any one of a synthetic cable, a steel cable, a belt, and a chain.

The powered actuator may also include a motor encoder adapted to measure angular displacement of a rotor of the motor with respect to a stator of the motor, and a joint encoder adapted to measure angular displacement of the joint about a joint pivot. The motor encoder, the joint encoder, or both may include an absolute encoder. The motor encoder and/or the joint encoder may also include a magnetic encoder having at least 13-bit resolution.

In another aspect, embodiments of the invention feature a method for augmenting joint function using a powered human augmentation device. The method includes modulating one or more of joint augmentation torque, joint impedance, and joint equilibrium during a phase of a gait cycle. The modulation is achieved, in part, using a motor having a dissipation constant less than about 50 W/(Nm)$^2$ and that is coupled directly to a transmission. The transmission is serially coupled to an elastic element that is coupled to the joint. The method includes energizing the motor to apply the augmentation torque to the joint during a phase of the gait cycle, such that the applied torque normalized by weight is in a range from about −2.8 Nm/kg up to about 2.8 Nm/kg. The transmission may have a gear ratio less than about 80:1.

In some embodiments, the method includes energizing the motor to apply stiffness (a component of the impedance) to the joint, so that energy is stored in the elastic element and power from release of the stored energy combines with the applied motor power to achieve a positive torque feedback response that approximates a muscle-tendon reflex. The method may also include energizing the motor to apply the torque to achieve a desired joint equilibrium, and subsequently shorting leads of the motor during a stance phase of the gait cycle to approximate a mechanical clutch, such that the joint equilibrium is substantially maintained during a portion of the stance phase.

In some embodiments, the method includes measuring angular displacement of a rotor of the motor with respect to a stator of the motor and measuring angular displacement of a structure with respect to the joint. The method also include determining a state of the elastic element based, at least in part, on both the angular displacement of the rotor and the angular displacement of the structure. Moreover, based at least in part on the state of the elastic element and the angular displacement on the motor, torque contribution of the motor is computed, and the modulation is adjusted, based at least in part on the computed contribution of the motor torque.

In another aspect, embodiments of the invention feature a method for supplying one or more of an augmentation torque, joint equilibrium, and an impedance to a joint augmented by a powered human augmentation device. The method includes directly coupling a motor having a dissipation constant less than about 50 W/(Nm)$^2$ to a transmission. The method also includes coupling an elastic element to both the joint and the transmission, whereby when the motor is energized to supply the augmentation torque, the torque applied to the joint normalized by weight is in a range from about −2.8 Nm/kg up to about 2.8 Nm/kg.

In some embodiments, the motor may include a high-torque motor supplying torque of at least about 0.06 Nm/kg. Alternatively, or in addition, the motor may include a low revolutions per minute (RPM) motor having an RPM less than about 1500, a transverse-flux motor, or both. The actuator may be adapted to be backdrivable.

In some embodiments, the transmission has a gear ratio less than about 80:1. The transmission may include a ball-screw transmission having a ball nut coupled to the elastic element. The ball-screw transmission may include a screw having a pitch in a range of about 2 mm up to about 10 mm, which can yield the gear ratio of less than about 80:1.

In some embodiments, the elastic element may include a spring, and the powered actuator may additionally include a cable and a joint output pulley. In those embodiments, the cable is coupled to both the spring and the joint output pulley. In some other embodiments, the transmission includes a ball-screw transmission having a ball nut coupled to the motor rotor and the screw is coupled to the elastic element.

In some embodiments, the motor of the powered actuator includes a motor having an external rotor, and the transmission includes a cable and a joint output pulley. The cable couples the external rotor and the joint output pulley. The cable may be any one of a synthetic cable, a steel cable, a belt, and a chain. The augmentation torque and/or the impedance may supplied to one or more of a hip joint, a knee joint, and an ankle joint.

These and other objects, along with advantages and features of the embodiments of the present invention herein disclosed, will become more apparent through reference to the following description, the accompanying drawings, and the claims. Furthermore, it is to be understood that the features of the various embodiments described herein are not mutually exclusive and can exist in various combinations and permutations. As used herein, the term "substantially" means about ±10% and, in some embodiments, about ±5%.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which:

FIG. 5 is a table of certain design and operating parameters of powered actuators according to various embodiments.

DESCRIPTION

The entire contents of each of U.S. patent application Ser. No. 12/157,727 "Powered Ankle-Foot Prosthesis" filed on Jun. 12, 2008 (Publication No. 2011/0257764 A1); U.S. patent application Ser. No. 12/552,013 "Hybrid Terrain-Adaptive Lower-Extremity Systems" filed on Sep. 1, 2009 (Publication No. US2010/0179668 A1); U.S. patent application Ser. No. 13/079,564 "Controlling Power in a Prosthesis or Orthosis Based on Predicted Walking Speed or Surrogate for Same" filed on Apr. 4, 2011; U.S. patent application Ser. No. 13/079,571. "Controlling Torque in a Prosthesis or Orthosis Based on a Deflection of Series Elastic Element" filed on Apr. 4, 2011; U.S. patent application Ser. No. 13/347,443 "Powered Joint Orthosis" filed on Jan. 10, 2012; co-pending U.S. patent application Ser. No. 13/356,230 "Terrain Adaptive Powered Joint Orthosis" filed on Jan. 23, 2012; and co-pending U.S. Provisional Patent Application Ser. No. 61/595,453 "Powered Ankle Device" filed on Feb. 6, 2012 are incorporated herein by reference.

Figure 1B:
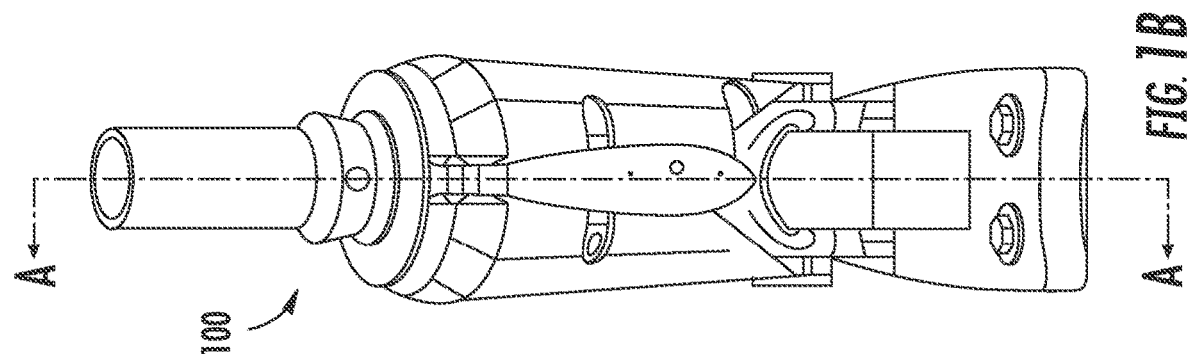
FIG. 1A-1C illustrate a powered actuator employing a ball-screw transmission, according to one embodiments for use with ankle prostheses.
Figure 1A:
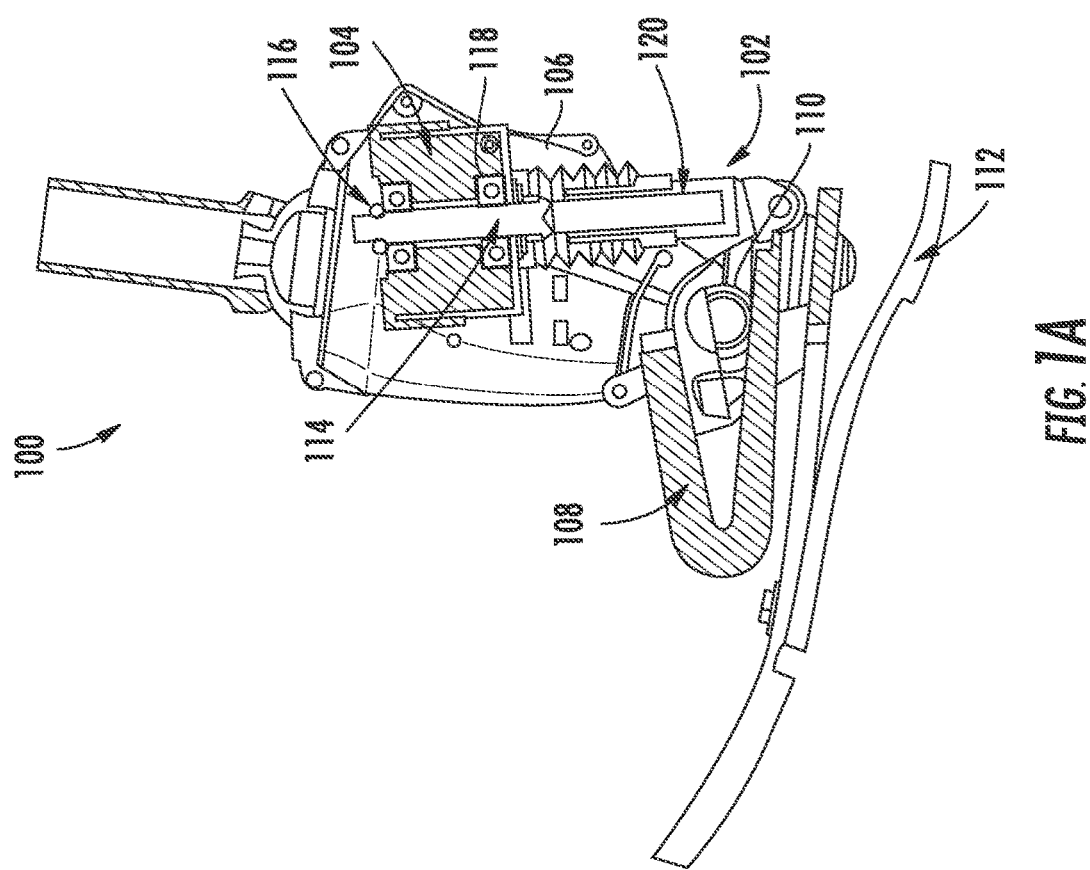

In various embodiments described below, die use of an SEA in a biomimetic ankle device is described for the sake of convenience. That SEA mechanism can be readily adapted for use with biomimetic knee and/or hip devices also. A biomimetic ankle-foot prosthesis 100 depicted in FIGS. 1A and 1B includes an SEA 102. The SEA 102 uses a direct-drive, ball-screw based transmission system in which an electric motor 104 is directly coupled to a ball-screw transmission 106, which is serially coupled to an elastic element 108, connecting the transmission 106 to a joint output, i.e., the ankle pivot 110. Thus, the SEA 102 applies torque via a robotic joint, i.e., the ankle pivot 110, to an output load, i.e., a carbon-fiber foot 112. In some embodiments, another elastic element may be connected between the motor 104 and the foot 112, in parallel to the serially connected elastic element 108.

The motor 104 is a high-torque, low-speed (rpm) motor, e.g., a transverse-flux motor, an "external rotor" permanent magnet motor, etc. Modern transverse-flux motors employ a high-pole-count external rotor (internal stator) and circumferentially-applied stator windings to achieve high-torque density with low winding resistance, thereby mitigating many of the typical disadvantages of using other high-torque motors in portable devices. These transverse flux motors are particularly suited for prosthetic/orthotic/exoskeletal/humanoid devices because they have a high power-to-weight ratio. Transverse flux motors also have lower peak-to-continuous power ratings compared to those of other motors, thereby enabling a prosthetic/orthotic/exoskeletal device to operate at high power levels for longer periods without reaching thermal limits. Transverse flux motors can also provide a significant motor dissipation reduction as defined by the motor copper loss per square unit of torque as defined by $R/k_t^2$, whereby R is the stator winding resistance in ohms, and $k_t$ is the motor torque constant measured in N-m/amp, thereby increasing motor efficiency. Lower frictional losses (generally due to the reduced number of motor revolutions per gait cycle) in the transmission further increase the overall efficiency of the prosthetic/orthotic/exoskeletal devices. The design life of the transmission can increase also, in part due to the reduction in motor revolutions per cycle. These benefits can be leveraged by the SEAs, such as the SEA 102, using ball-screw and cable transmissions.

Specifically, the rotor of the motor 104 is attached to a ball-screw shaft 114 using a clamping nut 116. The clamping nut applies a preload to the axial thrust bearings 118 that serve to align the ball-screw shaft 114 radially and support the thrust imparted by the ball nut 120 during actuation. The rotating screw 114 drives the ball-nut 120 longitudinally which in turn drives the series spring 108 about the ankle pivot beatings 110, thus providing impedance and/or torque at the ankle to the foot 112. Those skilled in the art appreciate that alternatively, in some embodiments, the rotor can be directly coupled to the ball-nut, thereby controlling the linear translation of the screw.

Typically in an ankle device, during the controlled dorsiflexion phase of the gait cycle, the SEA 102 delivers a programmable impedance and joint equilibrium at the ankle joint. It should be understood that in other devices, such as hip and/or knee devices, the SEA may deliver a programmable impedance, joint equilibrium, and/or torque in the controlled dorsiflexion and/or other phases of the gait cycle. In the ankle device 100, the SEA 102 thus emulates a non-linear (hardening) torsional spring impedance of the ankle pivot 110; the associated torque is stored as potential energy in the series spring 108. The hardening spring behavior can be accomplished through use of non-linear positive force or velocity feedback (as described in the various co-pending patent applications identified above) as a means of emulating the calf-muscle/Achilles tendon reflex response. At or near the end of the controlled dorsiflexion phase, the SEA 102 applies torque and, as the foot heel begins to lift off a surface on which the wearer is walking, the energy stored in the series spring 108 is released, like a catapult, combining with the motor applied torque to produce a positive force/torque feedback response to approximate a muscle-tendon reflex, thus producing at least a biomimetic response. The impedance and/or torque applied by the motor 104 may be normalized by the wearer's weight.

An absolute encoder may be used to measure angular displacement of the motor rotor in relation to the stator. Another absolute encoder may be used to measure angular displacement of the foot structure 112 about the ankle pivot bearings 110. Instead of absolute encoders, magnetic field angle encoders, e.g., the RMB-20 having a 13-bit resolution, manufactured by Renishaw, may be used. The measured angular displacements can be used to determine the state of the motor 104, for the purposes of commutation, torque, and/or joint equilibrium control, and of the output joint, i.e., ankle pivot 110. These motor and ankle states can be used to estimate the state of the series spring 108. (See for example, the co-pending U.S. patent application Ser. No. 13/079,564 "Controlling Power in a Prosthesis or Orthosis Based on Predicted Walking Speed or Surrogate for Same" filed on Apr. 4, 2011; U.S. patent application Ser. No. 13/079,571 "Controlling Torque in a Prosthesis or Orthosis Based on a Deflection of Series Elastic Element" filed on Apr. 4, 2011). In general, the motor position defines a joint equilibrium position through simple kinematics (e.g., the law of cosines). The difference between that joint equilibrium position and the actual joint position, when multiplied by a calibrated series spring constant, determines the series spring torque and, thereby, the energy stored in the spring.

In some embodiments, based on the determined series spring state and stiffness (i.e., spring constant) of the series spring 108, force and joint torque contribution of the SEA 102 is determined. Furthermore, based on the determined contribution of the spring force and motor torque, the torque and impedance applied by the SEA 102 and equilibrium of the joint can be modulated. (See for example, the co-pending U.S. patent application Ser. No. 13/347,443 "Powered Joint Orthosis" filed on Jan. 10, 2012; co-pending U.S. patent application Ser. No. 13/356,230 "Terrain Adaptive Powered Joint Orthosis" filed on Jan. 23, 2012; and co-pending U.S. Provisional Patent Application Ser. No. 61/595,453 "Powered Ankle Device" filed on Feb. 6, 2012).

The SEA 102 can achieve a low gear ratio, i.e., a ratio of the motor rotor displacement and the output joint displacement that is less than about 30:1 or about 20:1. In one embodiment of the SEA 102, the ball-Screw 114 typically delivers over about 2600 N of axial force at a screw pitch of 12 mm, delivering over 100 Nm of torque to the foot structure 112. A dissipation constant of the motor 104 across a range of gear ratios (e.g., from about 15:1 up to about 80:1) is less than about 50 Watts/(Nm)$^2$. The motor dissipation constant is a ratio of the total resistance R of the windings of the motor rotor and square of torque output by the motor per unit current supplied to the motor, denoted $k_t^2$.

In general, the torque output of a motor increases with the current drawn by the motor, which is related to the power supplied to the motor. However, the portion of the supplied power that is lost and dissipated as heat is proportional to the square of the current drawn by the motor. Therefore, as more power is supplied to a motor, the fraction of that power that increases the torque output of the motor can be less than the fraction that is wasted in the form of heat dissipation. Therefore, the motor 104, which has a low dissipation constant, i.e., $$\frac{R}{k_t^2}$$

less than about 50 W/(Nm)$^2$, can deliver high torque with low winding loss compared to other motors having a greater dissipation constant. As such, the motor 104 dissipates less heat, keeping the prosthesis 100 cool, and also requites less power, thereby increasing battery life.

In operation, in addition to providing torque to the ankle pivot 110 (e.g., at or near the end of the controlled dorsiflexion phase and/or in the powered plantar flexion phase of the gait cycle) the motor 104 may also provide an impedance and joint equilibrium to the ankle pivot 110, for example, to achieve an ankle (joint, in general) equilibrium trajectory during the swing phase of the gait cycle. Similarly, as in the application of torque as described above, the motor 104 can cause displacement of the ball nut 120, applying a force to the series spring 108 which, in turn, provides the required impedance to the ankle pivot 110 with respect to the joint equilibrium trajectory.

In some embodiments, the motor leads are shorted, such that the motor draws substantially no current and operates as a dynamic mechanical clutch. This can enable an ankle or other augmentation device to provide stability during loss of battery or system malfunction. The shorted leads mode exerts a viscous damping torque on the motor, proportional to $k_t^2/R$. As measured at the output of the transmission, the viscous damping is amplified by the square of the gear ratio, kg, yielding a transmission damping, B, of $kg^2 \times k_t^2/R$. For an SEA with series stiffness, $K_{SEA}$, the time constant of the dynamic (viscous) clutch is $B/K_{SEA}$. In some embodiments that store energy in the series spring for rapid release later, it is useful to apply the viscous clutch at a time when the desired spring energy is achieved. Within a small time period in relation to the time constant above, the transmission is effectively a static brake, enabling the spring to release and deliver power to the joint. Such a mode of operation is useful in slow walking, where consistent and quiet power is desired, and in running, where the ankle functions primarily as a spring, and the series spring release occurs in less than 50 milliseconds. Such a mode is also useful in control of a knee in early stance, to deliver high torque through the series spring with no battery power. In all of the above embodiments, the clutch is used to apply high torque but without substantially drawing energy from the battery.

Thus, in general, in an SEA having a certain gear ratio and a certain series spring constant, the smaller the motor dissipation constant the longer the duration for which the applied stiffness (a component of the impedance) can be substantially maintained after shorting the motor leads. Thus, in an SEA using a motor having a large dissipation constant and, consequently, having a duration for which stiffness can be substantially maintained without drawing current that is shorter than the time period for which the equilibrium needs to be maintained, the power supplied to the motor cannot be turned off without adversely affecting the joint (e.g., ankle) equilibrium. In the SEA 102, however, if the gear ratio of the transmission 106 is about 40:1, the motor dissipation constant is about 10, and the spring constant of the series spring 108 is about 400, the SEA 102 can maintain the applied stiffness for a time constant (i.e., holding time) of about 250 milliseconds. Typically during the stance phase of the gait cycle while walking or running, this holding time is sufficient to maintain a roughly fixed joint equilibrium for a required duration, typically about 50-100 milliseconds for walking and running. Accordingly, as the motor 104 draws substantially zero current after shorting the leads, a further reduction in the power consumption of the SEA 102 is achieved while simultaneously achieving ankle equilibrium.

Figure 1C:
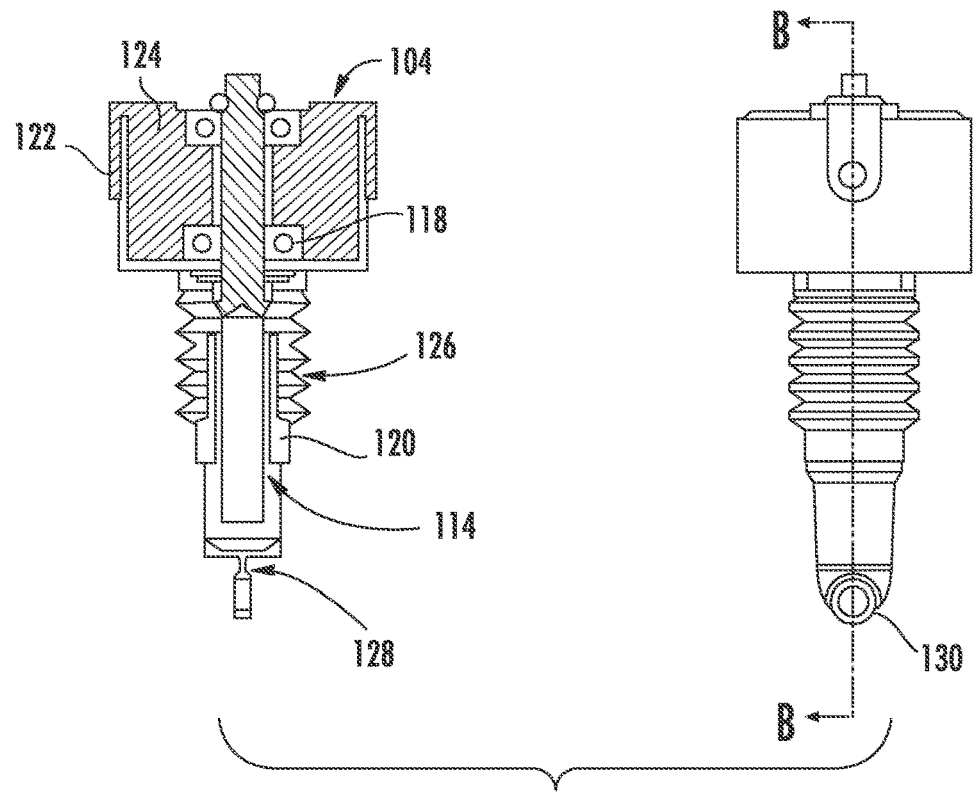

With reference to FIG. 1C, the three-phase stator assembly 122 of the motor 104 wraps around the rotor 124 to facilitate mounting of the motor to the prosthesis housing, e.g., using a needle bearing component. A bellows 126 protects the screw 114 from contamination. The ball-nut 120 employs an end-flexure 128 to isolate the thrust bearings 118 from out-of-plane moment loads as shown in Section A-A in FIG. 1B. The end-flexure 128 can move side-to-side so as to eliminate side-loads, further isolating the thrust bearings 118 from moments applied by the series spring 108. Typically, thrust loads on the end-flexure 128 are supported by needle bearings press fit into a end-flexure mounting hole 130.

Figure 2:
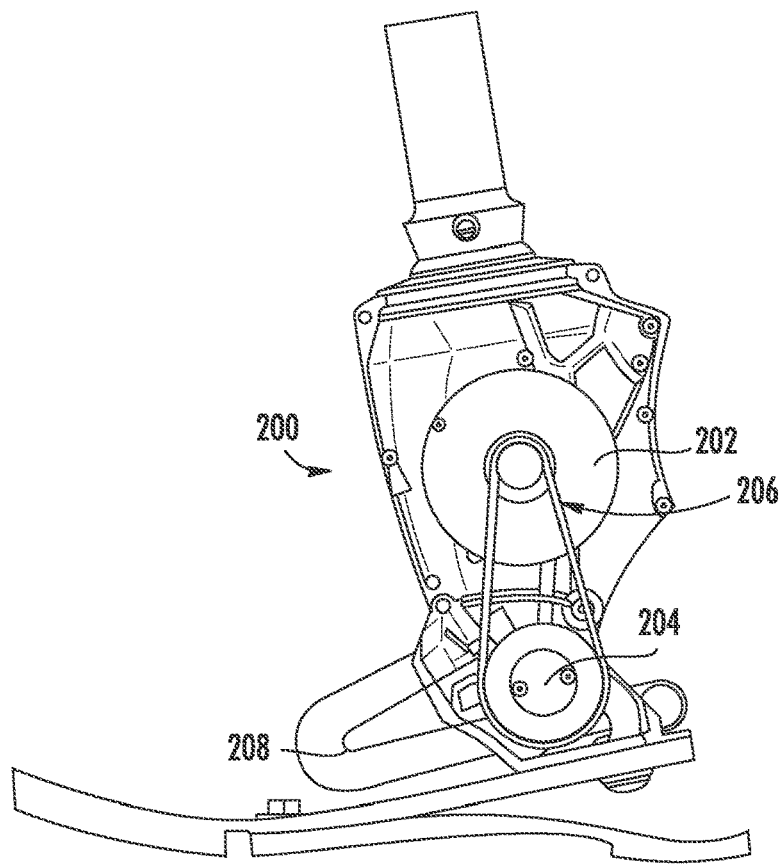
FIG. 2 illustrates a powered actuator employing a cable transmission, according to one embodiment, for use with ankle prostheses.

FIG. 2 depicts a biomimetic ankle-foot prosthesis that uses a direct-drive rotary actuator 200 with a cable transmission. The actuator 200 employs a high-torque, transverse-flux, external rotor motor 202 to directly drive the ankle output pulley 204 via a cable 206. The cable can be a synthetic cable or a steel cable. In some embodiments, a belt of a chain drive may be used instead of a synthetic or steel cable. Motors other than transverse flux motors, but having an external rotor may also be used. A rotary series spring connects the ankle output pulley 204 to the ankle output joint 208. The rotor of the motor 202 may be captivated by ankle shells using needle bearings.

Absolute angular displacement of the ankle output pulley 204 and of the rotor of the motor 202 may be used, as described above with reference to FIGS. 1A and 1B to determine the state of the actuator 200. Magnetic field angle encoders may be used instead of absolute encoders. The flex in the cable 206 may be measured based on the span (length) of the cable, which is related to the difference between the output joint position and the motor position. With high resolution encoders, cable stretch can be sensed with sufficient bandwidth and resolution for closed-loop control. The flex in the cable 206 can then be compensated in an output torque feedback loop. The cable 206 in the actuator 200 can achieve a gear ratio, i.e., the ratio of the motor angle and the angle of the output joint, i.e., ankle pivot 208, of about 20:1, in one embodiment.

Figure 3A:
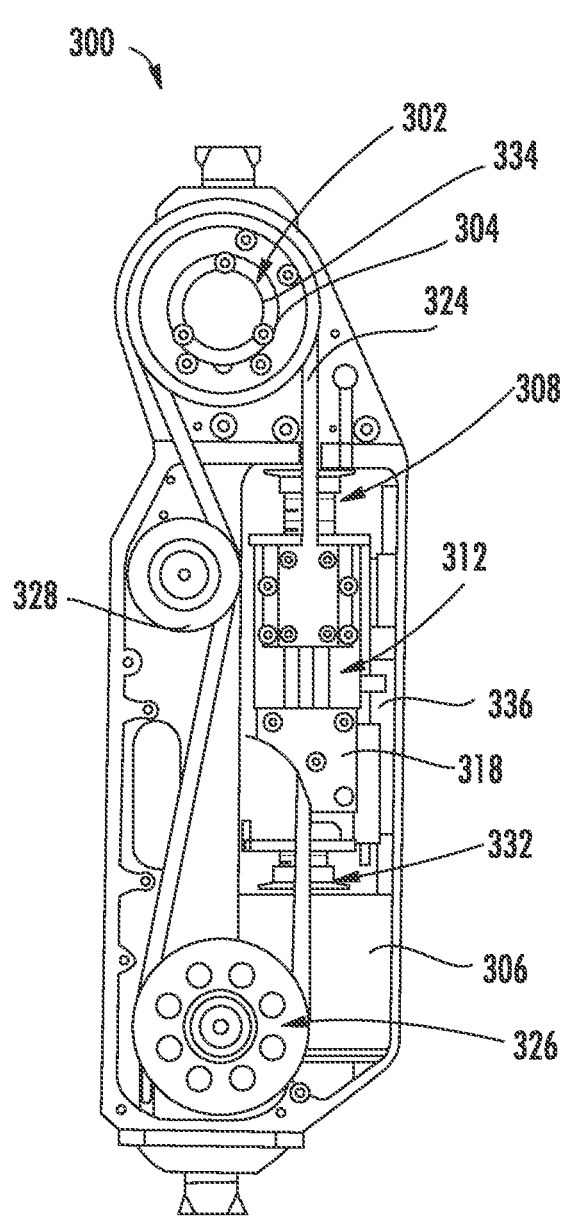
FIGS. 3A-3C illustrate a powered actuator employing a ball-screw transmission, according to one embodiment, for use with knee prostheses.
Figure 3B:
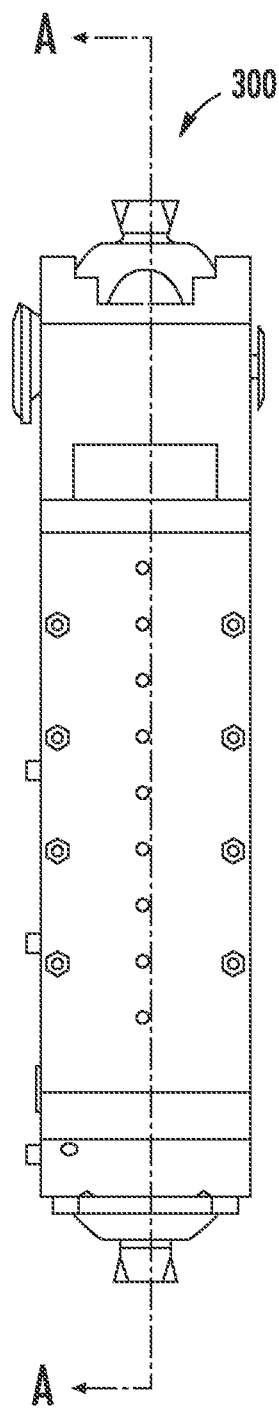
Figure 3C:
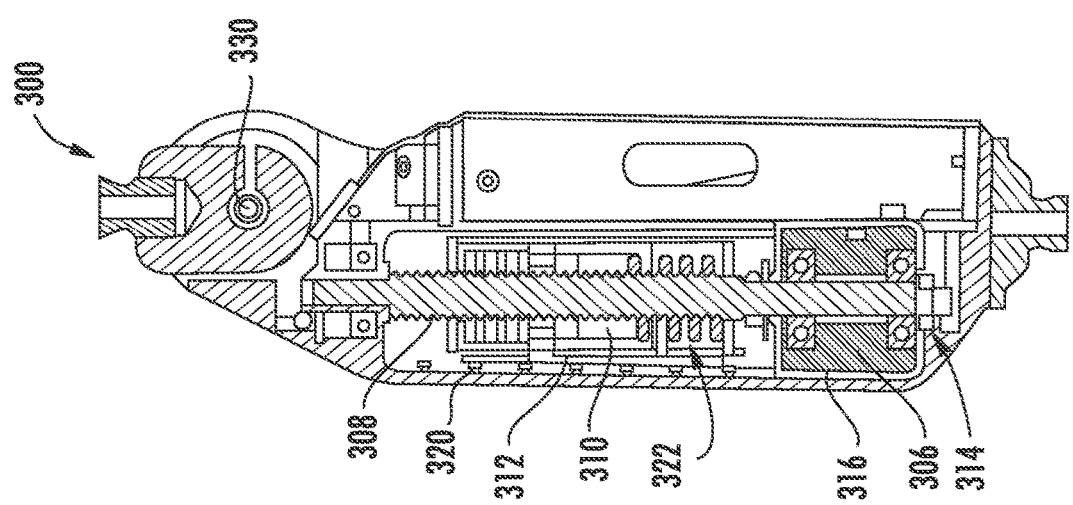

FIGS. 3A-3C illustrate a biomimetic knee prosthesis 300 that uses a direct-drive, ball-screw based system coupled to a series spring connecting the ball-screw transmission to the knee joint output. The device 300 controls the equilibrium position of the knee joint 302, and applies torque or impedance to the knee joint 302 substantially along the centerline of the output pulley 304. The knee prosthesis 300 can deliver about 200 Mm of torque over a range of about 120 degrees of angular displacement of the artificial knee joint 302 useful for stair and steep ramp ascent as well as for level ground walking. A transverse-flux, motor 306 (or other high-torque, external rotor motor) drives a screw 308 thereby driving a ball-nut 310 supported by a linear rail 312. A retaining nut 314 preloads the angular contact bearings 316 inside the motor 306.

A cable attachment device 318, also supported by the linear rail 312, connects to the ball-nut 310 via series springs 320, 322 and linearly drives the cable 324. The cable 324 wraps around a light-weight pulley 326, an idler pulley 328, and the output pulley 304 to apply torque/impedance to the knee joint 302 about the knee axis 330. The cable 324 can be a synthetic cable, a steel cable, a belt, or a chain drive.

The pitch of the ball screw 308 is in the range of approximately 6 mm up to about 10 mm so as to achieve a low gear ratio of less than about 30:1, of less than about 20:1. The gear ratio is a ratio of the respective angular displacements of the rotor of motor 306 and the knee joint 302. An absolute magnetic encoder 330 having at least a 13-bit resolution (e.g. RMB-20 manufactured by Renishaw), is used to measure the angular displacement of the motor rotor in relation to the stator, and an absolute magnetic encoder 334, which may also have at least a 13-bit resolution, is used to measure the angular displacement of the lower knee structure relative to the upper knee structure. The motor and knee joint angles are used, respectively, to determine the states of the motor 306 and the knee 302, and can also be used to estimate the state of the series springs 320, 322. For redundancy in sensing, a linear series-spring deflection potentiometer 336 is optionally included to measure series-spring deflections directly. Based on the series spring state and stiffness (i.e. spring constant), series-elastic actuator force and joint torque supplied by the SEA can be determined. (See for example, the co-pending U.S. patent application Ser. No. 13/079,564 "Controlling Power in a Prosthesis or Orthosis Based on Predicted Walking Speed or Surrogate for Same" filed on Apr. 4, 2011; U.S. patent application Ser. No. 13/079,571 "Controlling Torque in a Prosthesis or Orthosis Based on a Deflection of Series Elastic Element" filed on Apr. 4, 2011).

Figure 4:
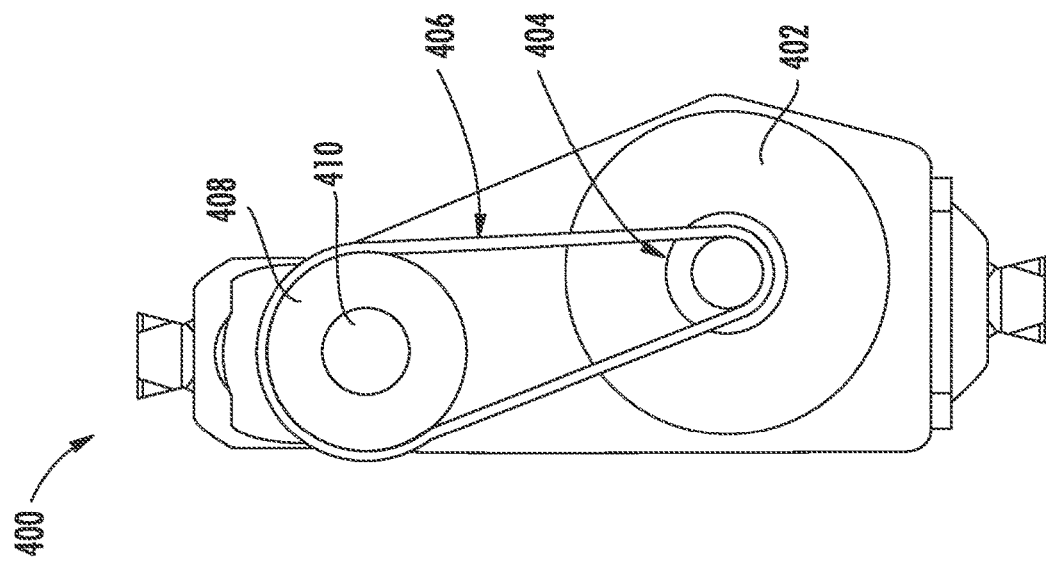
FIG. 4 illustrates a powered actuator employing a cable transmission, according to one embodiment, for use with knee prostheses.

FIG. 4 depicts a biomimetic knee prosthesis that uses a direct-drive rotary actuator 400 using cable transmission, similar to that described above with reference to FIG. 2. A high-torque external rotor motor 402 (e.g., a transverse flux motor) is configured in a "pancake" arrangement to minimize stack height and to maximize torque-current gain. The motor 402 drives a pulley 404 and, through a direct-cable transmission 406, drives the output pulley 408. A rotary series spring couples the knee output pulley 408 to the knee output joint 410. Thus, rotating the output pulley 408, in turn, causes the knee joint 410 to rotate. Absolute encoders on the motor 403 and on the output pulley 408 may be used to measure the state of the actuator 400 similarly as described above with reference to FIGS. 1A and 1B. The SEA 400 yields a low gear ratio, i.e., the ratio of the motor angle and the knee joint angle, of about 20:1.

Although various direct-drive SEAs are described above as components of wearable robot ankle and knee prosthetic devices, this is for illustrative purposes only. Hip prosthetic devices are also contemplated. To those skilled in the art, it should be apparent that these SEAs can be readily adapted for use in wearable robot ankle, knee, and hip orthotic devices, wearable robots for upper-extremity orthotic and prosthetic devices, and in humanoid robots. It should also be understood that although the powered actuators described herein take advantage of some of the key attributes of transverse flux motors, specifically high torque density and efficiency, these actuators can also leverage other high-torque motors, including hybrid stepping motors, induction motors, traditional radially-applied permanent magnet motors, and variable reluctance motors. The speed of these motors may be less than 5000 rpm, or less than 1500 rpm, or less than 300 rpm, depending on the optimum system design as defined by the motor, transmission gear ratio, series-spring stiffness, parallel elasticity, and battery power source; optimum generally referring to a tradeoff of battery economy per stride, design life of the transmission, and device weight. Table 1 in FIG. 5 shows various design and operating parameters of the powered SEAs according to various embodiments. The minimum, typical, and maximum values of these parameters are also listed in Table 1. A typical wearer weighs in the range from about 190 lbs up to about 250 lbs. Wearer mass is used to normalize the actuator weight. Series Stiffness (i.e., spring constant of the serially connected elastic element) and Parallel Stiffness (i.e., spring constant of the optional elastic element connected in parallel with the serially connected elastic element).

While the invention has been particularly shown and described with reference to specific embodiments, it will be understood by those skilled in the art that various changes in form and detail may be made therein without departing from the spirit and scope of the invention as defined by the appended claims. The scope of the invention is thus indicated by the appended claims and all changes that come within the meaning and range of equivalency of the claims are therefore intended to be embraced.

What is claimed is:

1. A powered human augmentation device comprising:
a low revolutions-per-minute (RPM) motor having an RPM less than 1500 configured to apply torque to a joint of the human augmentation device during a phase of a gait cycle to modulate at least one of joint augmentation torque, joint impedance, or joint equilibrium during the phase of the gait cycle;
a transmission coupled directly to the low RPM motor; and
a controller configured to short leads of the motor to exert a viscous damping torque on the motor proportional to a motor dissipation constant given by $R/k_t^2$, where R refers to a stator winding resistance and $k_t$ refers to a motor torque constant, the dissipation constant being less than 50 W/(Nm)$^2$.

2. The device of claim 1, wherein the motor comprises a high-torque motor supplying motor torque of at least about 0.06 Nm/kg.

3. The device of claim 1, wherein the device is adapted to be backdrivable.

4. The device of claim 1, wherein the transmission has a gear ratio less than about 80:1.

5. The device of claim 1, wherein:
the motor comprises an external rotor; and
the transmission comprises a cable and a joint output pulley, the cable coupling the external rotor and the joint output pulley.

6. The device of claim 1, further comprising:
a motor encoder adapted to measure angular displacement of a rotor of the motor with respect to a stator of the motor; and
a joint encoder adapted to measure angular displacement of the joint about a joint pivot.

7. The device of claim 6, wherein at least one of the motor encoder and the joint encoder is selected from a group comprising: an absolute encoder, or a magnetic encoder having at least 13-bit resolution.

8. A method for augmenting joint function using a powered human augmentation device, the method comprising:
energizing a low revolutions-per-minute (RPM) motor having an RPM less than 1500 to apply torque to a joint of the human augmentation device during a phase of a gait cycle to modulate at least one of joint augmentation torque, joint impedance, or joint equilibrium during the phase of the gait cycle, the motor coupled directly to a transmission; and
shorting leads of the motor to exert a viscous damping torque on the motor proportional to a motor dissipation constant given by $R/k_t^2$, where R refers to a stator winding resistance and $k_t$ refers to a motor torque constant, the dissipation constant being less than 50 W/(Nm)$^2$.

9. The method of claim 8, wherein the viscous damping torque is exerted on the motor during a loss of battery power.

10. The method of claim 8, wherein the dissipation constant is about 10 W/(Nm)2.

11. The method of claim 8, further comprising energizing the motor to apply stiffness to the joint, the elastic element configured to store energy and to release the stored energy as power, the motor applying power to augment the power of the elastic element to achieve a positive torque feedback response.

12. The method of claim 8, further comprising:
energizing the motor to apply the torque to achieve a desired joint equilibrium position; and
shorting leads of the motor during a stance phase of the gait cycle to substantially maintain the joint equilibrium position during a portion of the stance phase.

13. The method of claim 8, further comprising:
measuring an angular displacement of a rotor of the motor with respect to a stator of the motor;
measuring an angular displacement of a structure with respect to the joint;
determining, using a hardware controller, a state of the elastic element based, at least in part, on both the angular displacement of the rotor and the angular displacement of the structure;
computing, based at least in part on the state of the elastic element and the angular displacement of the motor, a torque contribution of the motor using the hardware controller; and
adjusting the modulating, based at least in part on the computed contribution of the motor torque.

14. A powered human augmentation device comprising:
a low revolutions-per-minute (RPM) motor having an RPM less than 1500 configured to apply torque to a joint of the human augmentation device during a phase of a gait cycle to modulate at least one of joint augmentation torque, joint impedance, or joint equilibrium during the phase of the gait cycle;
a transmission coupled directly to the low RPM motor;
an elastic element serially coupled to the transmission, the elastic element coupled to the joint; and a controller configured to short leads of the motor to exert a viscous damping torque on the motor.

15. The device of claim 14, wherein the elastic element comprises a spring, the device further comprising a cable and a joint output pulley, the cable being coupled to both the spring and the joint output pulley.

16. The device of claim 14, wherein the transmission comprises a ball-screw transmission having a ball nut coupled to the motor rotor and the screw coupled to the elastic element.

17. The device of claim 14, wherein the motor comprises a high-torque motor supplying motor torque of at least about 0.06 Nm/kg.

18. The device of claim 14, wherein the device is adapted to be backdrivable.

19. The device of claim 14, wherein the transmission has a gear ratio less than about 80:1.

20. The device of claim 14, further comprising:
a motor encoder adapted to measure angular displacement of a rotor of the motor with respect to a stator of the motor; and
a joint encoder adapted to measure angular displacement of the joint about a joint pivot.

\* \* \* \* \*